United States Patent
Chou et al.

(10) Patent No.: US 9,767,554 B2
(45) Date of Patent: Sep. 19, 2017

(54) METHOD AND SYSTEM FOR DETECTION OF SURGICAL GAUZE DURING ANATOMICAL SURGERY

(71) Applicant: SONY CORPORATION, Tokyo (JP)

(72) Inventors: Chen-Rui Chou, San Jose, CA (US); Ming-Chang Liu, San Jose, CA (US)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 14/855,525

(22) Filed: Sep. 16, 2015

(65) Prior Publication Data
US 2016/0247275 A1 Aug. 25, 2016

Related U.S. Application Data

(60) Provisional application No. 62/118,030, filed on Feb. 19, 2015.

(51) Int. Cl.
G06T 7/00 (2017.01)
G06K 9/46 (2006.01)
(Continued)

(52) U.S. Cl.
CPC .............. G06T 7/0012 (2013.01); A61B 5/06 (2013.01); G06K 9/4609 (2013.01);
(Continued)

(58) Field of Classification Search
CPC .. G06K 9/4609; G06K 9/4652; G06K 9/6218; G06K 2209/057; G06T 7/0012;
(Continued)

(56) References Cited

U.S. PATENT DOCUMENTS

| 8,181,860 B2 * | 5/2012 | Fleck | A61B 90/37 235/380 |
| 8,983,167 B2 * | 3/2015 | Satish | G01N 21/25 382/134 |

(Continued)

FOREIGN PATENT DOCUMENTS

WO 2014/045026 A 3/2014

OTHER PUBLICATIONS

International Search Report and the Written Opinion received for PCT Application No. PCT/US2016/017446, mailed on May 2, 2016, p. 12.

(Continued)

*Primary Examiner* — Katrina Fujita
(74) *Attorney, Agent, or Firm* — Chip Law Group

(57) ABSTRACT

Various aspects of a method and system for detection of surgical gauze during anatomical surgery are disclosed herein. In accordance with an embodiment of the disclosure, the method is implementable in an image-processing engine, which is communicatively coupled to an image-capturing device that captures one or more video frames. The method includes the determination of a set of pixel characteristics based on color filtering of at least a portion of a video frame. Thereafter, one or more blocks of pixels of a portion of a surgical gauze are detected in the video frame based on the set of pixel characteristics. Further, additional pixels that correspond to a remaining portion of the surgical gauze are identified based on a plurality of metrics. The surgical gauze is recognized in the video frame based on the detection of the one or more blocks of pixels and the identification of the additional pixels.

22 Claims, 7 Drawing Sheets

(51) Int. Cl.
*A61B 5/06* (2006.01)
*G06K 9/62* (2006.01)
*H04N 5/232* (2006.01)
*G06T 7/11* (2017.01)
*G06T 7/187* (2017.01)

(52) U.S. Cl.
CPC ......... *G06K 9/4652* (2013.01); *G06K 9/6218* (2013.01); *G06T 7/11* (2017.01); *G06T 7/187* (2017.01); *H04N 5/232* (2013.01); *H04N 5/23229* (2013.01); *G06K 2209/057* (2013.01); *G06T 2207/10024* (2013.01); *G06T 2207/10068* (2013.01); *G06T 2207/30004* (2013.01); *H04N 5/23216* (2013.01); *H04N 5/23293* (2013.01)

(58) Field of Classification Search
CPC ......... G06T 7/0085; G06T 7/11; G06T 7/187; G06T 2207/10024; G06T 2207/10068; G06T 2207/30004; H04N 5/232; H04N 5/23216; H04N 5/23229; H04N 5/23293; A61B 5/06
See application file for complete search history.

(56) References Cited

U.S. PATENT DOCUMENTS

| | | | | |
|---|---|---|---|---|
| 9,070,192 | B1* | 6/2015 | Smith | G06K 9/4652 |
| 9,171,368 | B2* | 10/2015 | Satish | G01N 21/25 |
| 9,595,104 | B2* | 3/2017 | Satish | G01N 21/25 |
| 2006/0207066 | A1 | 9/2006 | Segelke et al. | |
| 2007/0014467 | A1* | 1/2007 | Bryll | G06K 9/4609 |
| | | | | 382/152 |
| 2008/0181496 | A1* | 7/2008 | Ferman | G06K 9/00456 |
| | | | | 382/168 |
| 2009/0317002 | A1 | 12/2009 | Dein | |
| 2011/0311129 | A1* | 12/2011 | Milanfar | G06K 9/00335 |
| | | | | 382/154 |
| 2013/0010094 | A1 | 1/2013 | Satish et al. | |
| 2013/0011042 | A1* | 1/2013 | Satish | G06K 9/00 |
| | | | | 382/134 |
| 2013/0301901 | A1* | 11/2013 | Satish | G01N 21/25 |
| | | | | 382/134 |
| 2013/0303870 | A1* | 11/2013 | Satish | A61B 5/14535 |
| | | | | 600/371 |
| 2014/0063272 | A1 | 3/2014 | Tsuchida et al. | |
| 2014/0126788 | A1 | 5/2014 | Satish et al. | |
| 2014/0294299 | A1* | 10/2014 | Kim | G06T 5/002 |
| | | | | 382/167 |
| 2015/0154751 | A1* | 6/2015 | Satish | G01N 21/25 |
| | | | | 382/128 |
| 2016/0027173 | A1* | 1/2016 | Satish | G01N 21/25 |
| | | | | 382/128 |
| 2016/0071264 | A1* | 3/2016 | Agam | G06T 7/0012 |
| | | | | 382/128 |
| 2016/0094829 | A1* | 3/2016 | Georgiev | H04N 13/0022 |
| | | | | 348/43 |

OTHER PUBLICATIONS

Shamik Sural et al., "A Histogram with Perceptually Smooth Color Transition for Image Retrieval", Fourth International Conference on Computer Vision, Pattern Recognition and Image Processing, 2002, pp. 4.

D S Guru et al., "Texture Feature and KNN in Classification of Flower Images", IJCA Special Issue on "Recent Trends in Image Processing and Pattern Recognition", RTIPPR, 2010, p. 21-29.

M. Emre Celebi, "Distance Measure for Reduced Ordering Based Vector Filters", IET Image Processing, vol. 3 Issue 5 (pp. 249-260, Oct. 2009), Sep. 7, 2010, p. 12.

Kevin W. Duke, "A Study of the Relationship between Spectrum and Geometry through Fourier frames and Laplacian Eigenmapes", Dissertation submitted to the Faculty of the Graduate School of the University of Maryland, College Park in partial fulfillment of the requirements for the degree of Doctor of Philosophy, 2012, pp. 43.

* cited by examiner

METHOD AND SYSTEM FOR DETECTION OF SURGICAL GAUZE DURING ANATOMICAL SURGERY

CROSS-REFERENCE TO RELATED APPLICATIONS/INCORPORATION BY REFERENCE

This application claims priority to U.S. Provisional Patent Application Ser. No. 62/118,030 filed on Feb. 19, 2015, the entire content of which is hereby incorporated by reference.

FIELD

Various embodiments of the disclosure relate to a method and system for detection of surgical gauze. More specifically, various embodiments of the disclosure relate to a method and system for detection of surgical gauze during anatomical surgery.

BACKGROUND

With recent advancements in the medical sciences, various surgical and diagnostic procedures can now be performed by use of minimally invasive techniques. Such minimally invasive techniques may require small incisions to insert endoscopic or laparoscopic surgical instruments through the patient's skin into the body cavity. The endoscopic or laparoscopic surgical instruments may include an inbuilt camera to capture video footage of the body cavity. The video footage may be displayed to a physician in real time to enable the physician to perform the surgical or diagnostic procedure on a designated anatomical region within the body cavity. In certain scenarios, one or more surgical gauzes may be used during the surgical or diagnostic procedure. For instance, surgical gauze may be placed in the body cavity around the anatomical region to absorb blood and other body fluids that may ooze during the surgical or diagnostic procedure. However, surgical gauze may pose a risk to the patient if it remains inside the body cavity after the completion of the surgical or diagnostic procedure. Hence, there is a need for real-time analysis of video footage of surgical or diagnostic procedures to detect and monitor surgical gauze in the body cavity throughout the anatomical region.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

A method and system to detect surgical gauze during anatomical surgery substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
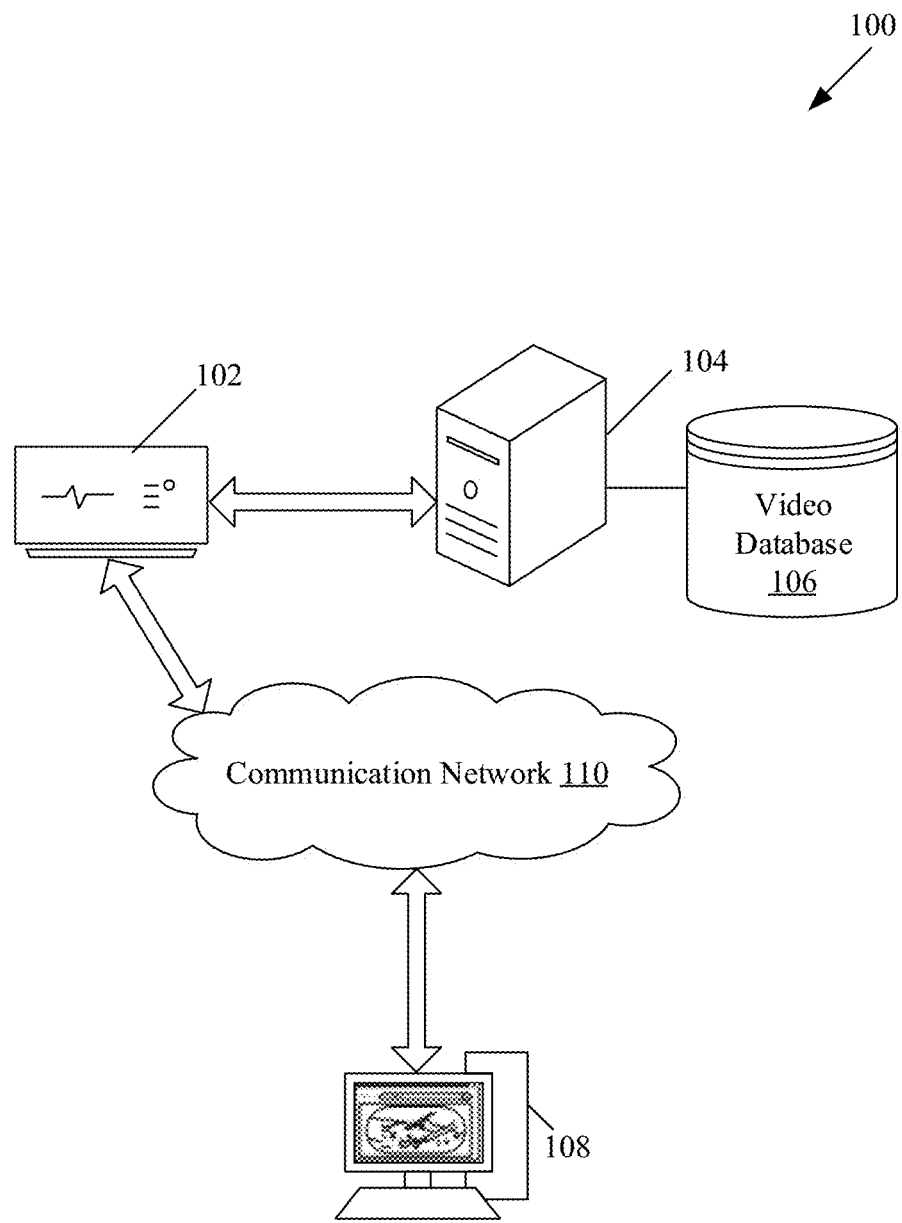
FIG. 1 is a block diagram that illustrates a network environment, in accordance with an embodiment of the disclosure.

The following described implementations may be found in the disclosed method and system for detection of surgical gauze during anatomical surgery. Exemplary aspects of the disclosure may include a method implementable in an image-processing engine. The image-processing engine may be communicatively coupled to an image-capturing device. The image-capturing device may be configured to capture one or more video frames. The method may include the determination of a set of pixel characteristics based on color filtering performed on at least a portion of a video frame received from the image-capturing device. Thereafter, one or more blocks of pixels that correspond to a portion of surgical gauze in the portion of the video frame may be detected based on the determined set of pixel characteristics. Further, additional pixels that may correspond to a remaining portion of the surgical gauze may be identified based on a plurality of metrics. The surgical gauze may then be recognized in the portion of the video frame based on the detection of the one or more blocks of pixels and the identification of the additional pixels.

In accordance with an embodiment, the set of pixel characteristics may include, but are not limited to, an edge feature, a shape feature, a texture feature, a size feature, a color feature, an intensity feature, and/or a density feature. In accordance with an embodiment, the plurality of metrics may comprise at least a spatial metric and a spectral metric. The spatial metric may correspond to a geometric distance between coordinates of two pixels in the portion of the video frame. Further, the spectral metric may correspond to a lighting-invariant color metric. The lighting-invariant color metric may correspond to a cosine distance between color components of two pixels in the portion of the video frame.

In accordance with an embodiment, the spatial metric, the spectral metric, and a weighting parameter may be combined to determine a Euclidean distance between two pixels in the portion of the video frame. In accordance with an embodiment, the additional pixels may be identified by use of a k-means clustering technique based on the combination of the spatial metric, the spectral metric, and a weighting parameter.

In accordance with an embodiment, the one or more blocks that correspond to the portion of the surgical gauze may be detected based on a connected component analysis of at least a portion of the video frame. In accordance with an embodiment, one or more pixel clusters may be determined in the video frame, based on a super-pixel clustering technique. The identification of the additional pixels may comprise selection of at least one pixel cluster from the one or more pixel clusters. Further, the recognition of the surgical gauze in the portion of the video frame may be based on the selected at least one pixel cluster.

In accordance with an embodiment, one or more image-capture settings of the image-capturing device may be adjusted based on the recognition of the surgical gauze in the portion of the video frame. Examples of the one or more image-capture settings may include, but are not limited to, auto-exposure, auto-focus, auto-white-balance, or auto-illumination.

In accordance with an embodiment, at least a portion of the video frame may be displayed to a user (such as a physician) via a user interface (UI) during the surgical procedure in real-time. The recognized surgical gauze may be masked or highlighted in the portion of the video frame displayed to the user via the UI. In accordance with an embodiment, a notification indicative of the recognition of the surgical gauze may be generated. Examples of the notification may include, but are not limited to, an audio alert, a textual alert, a visual alert, or a haptic alert.

FIG. 1 is a block diagram that illustrates a network environment, in accordance with an embodiment of the disclosure. With reference to FIG. 1, there is shown a network environment 100. The network environment 100 may include a surgical device 102, an image-processing server 104, a video database 106, a user terminal 108, and a communication network 110. The surgical device 102 may be communicatively coupled with the image-processing server 104, the video database 106, and the user terminal 108, via the communication network 110.

The surgical device 102 may comprise suitable logic, circuitry, interfaces, and/or code that may be configured to perform one or more surgical procedures and/or diagnostic analyses associated with one or more anatomical regions of a patient. Examples of the surgical device 102 may include, but are not limited to, a minimally invasive surgical/diagnostic device, a minimal incision surgical/diagnostic device, and/or an endoscopic/laparoscopic surgical/diagnostic device.

In accordance with an embodiment, the surgical device 102 may further include an image-capturing device (not shown in FIG. 1). The image-capturing device may capture one or more video frames of an anatomical region of a patient when a surgery or diagnostic procedure is performed on the anatomical region. Alternatively, the surgical device 102 may be communicatively coupled to the image-capturing device, via the communication network 110. Examples of the image-capturing device may include, but are not limited to, an endoscopic/laparoscopic camera, an ultrasound-based camera, a medical resonance imaging (MRI) device, a computer tomography (CT) scanning device, a minimally invasive medical imaging device, and/or a minimal incision medical imaging device.

The image-processing server 104 may comprise one or more servers that may provide an image-processing service to one or more subscribed electronic devices, such as the user terminal 108 and/or the surgical device 102. In accordance with an embodiment, the image-processing server 104 may be configured to analyze the one or more video frames captured by the image-capturing device while the surgical or diagnostic procedure is performed. The image-processing server 104 may then recognize surgical gauze in at least one of the one or more video frames, based on the analysis of the one or more video frames. In accordance with an embodiment, the image-processing server 104 may be implemented as a plurality of cloud-based resources by use of several technologies that are well known to those skilled in the art. Further, the image-processing server 104 may be associated with a single or multiple service providers. Examples of the one or more servers may include, but are not limited to, Apache™ HTTP Server, Microsoft® Internet Information Services (IIS), IBM® Application Server, Sun Java™ System Web Server, and/or a file server.

A person with ordinary skill in the art will understand that the scope of the disclosure is not limited to implementation of the image-processing server 104 and the surgical device 102 as separate entities. In accordance with an embodiment, the functionalities of the image-processing server 104 may be implemented by the surgical device 102, without departure from the scope of the disclosure.

The video database 106 may store a repository of one or more video frames captured by the image-capturing device. In accordance with an embodiment, the video database 106 may be communicatively coupled to the image-processing server 104. The video database 106 may receive the video frames, via the image-processing server 104, when the video frames are captured by the image-capturing device. In accordance with an embodiment, the video database 106 may be implemented by use of various database technologies known in the art. Examples of the video database 106 may include, but are not limited to, Microsoft® SQL Server, Oracle®, IBM DB2®, Microsoft Access®, PostgreSQL®, MySQL®, and/or SQLite®. In accordance with an embodiment, the image-processing server 104 may connect to the video database 106, based on one or more protocols. Examples of such one or more protocols may include, but are not limited to, Open Database Connectivity (ODBC)® protocol and Java Database Connectivity (JDBC)® protocol.

A person with ordinary skill in the art will understand that the scope of the disclosure is not limited to implementation of the image-processing server 104 and the video database 106 as separate entities. In accordance with an embodiment, the functionalities of the video database 106 may be implemented by the image-processing server 104, without departure from the spirit of the disclosure.

The user terminal 108 may comprise suitable logic, circuitry, interfaces, and/or code that may be configured to present a user interface (UI) to display the video frame to a user, such as a physician. In accordance with an embodiment, the user terminal 108 may display the video frame, in real time, while the surgical or diagnostic procedure is performed on the anatomical region of the patient. The user terminal 108 may be further configured to display the surgical gauze that is detected in the video frame by the image-processing server 104. Examples of the user terminal 108 may include, but are not limited to, a smartphone, a camera, a tablet computer, a laptop, a wearable electronic device, a television, an Internet Protocol Television (IPTV), and/or a Personal Digital Assistant (PDA) device.

A person with ordinary skill in the art will understand that the scope of the disclosure is not limited to implementation of the user terminal 108 and the image-processing server 104 as separate entities. In accordance with an embodiment, the functionalities of the image-processing server 104 may be implemented by the user terminal 108, without departure from the spirit of the disclosure. For example, the image-processing server 104 may be implemented as an application program that runs and/or is installed on the user terminal 108.

A person skilled in the art will understand that in accordance with an embodiment, the user terminal 108 may be integrated with the surgical device 102. Alternatively, the user terminal 108 may be communicatively coupled to the surgical device 102 and a user of the user terminal 108, such as a physician, may control the surgical device 102, via the UI of the user terminal 108.

The communication network 110 may include a medium through which the surgical device 102 and/or the user terminal 108 may communicate with one or more servers, such as the image-processing server 104. Examples of the communication network 110 may include, but are not limited to, the Internet, a cloud network, a Wireless Fidelity (Wi-Fi) network, a Wireless Local Area Network (WLAN), a Local Area Network (LAN), a plain old telephone service (POTS), and/or a Metropolitan Area Network (MAN). Various devices in the network environment 100 may be configured to connect to the communication network 110, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, and/or Bluetooth (BT) communication protocols.

In operation, the image-processing server 104 may be configured to determine a set of pixel characteristics of pixels in a video frame, which may be captured by the image-capturing device. Examples of the pixel characteristics may include, but are not limited to, an edge feature, a shape feature, a texture feature, a size feature, a color feature, an intensity feature, and/or a density feature. In accordance with an embodiment, the determination of the set of pixel characteristics may be based on color filtering performed on at least a portion of the video frame.

In accordance with an embodiment, the image-processing server 104 may be further configured to detect one or more blocks of pixels that correspond to a portion of surgical gauze in the video frame base on the determined set of pixel characteristics. Thereafter, the image-processing server 104 may be configured to identify additional pixels for a remaining portion of the surgical gauze based on a plurality of metrics. In accordance with an embodiment, the plurality of metrics may comprise at least a spatial metric and a spectral metric. The spatial metric may correspond to a geometric distance between coordinates of two pixels in the video frame. Further, the spectral metric may correspond to a lighting-invariant color metric. The lighting-invariant color metric may correspond to a cosine distance between color components of two pixels in the video frame. Further, the image-processing server 104 may be configured to recognize the surgical gauze in the video frame, based on the detection of the one or more blocks of pixels and the identification of the additional pixels.

In accordance with an embodiment, the image-processing server 104 may be further configured to determine a Euclidean distance between two pixels in the video frame based on the spatial metric, the spectral metric, and a weighting parameter. Notwithstanding, the disclosure may not be so limited and the image-processing server 104 may combine the spatial metric, the spectral metric, and a weighting parameter to determine the distance between two pixels in the video frame using other mathematical functions known in the art, without deviation from the scope of the disclosure. In accordance with an embodiment, the image-processing server 104 may identify the additional pixels by use of a k-means clustering technique, based on the determined Euclidean distance.

In accordance with an embodiment, the image-processing server 104 may be configured to detect the one or more blocks that correspond to the portion of the surgical gauze, based on a connected component analysis of at least a portion of the video frame. In accordance with an embodiment, the image-processing server 104 may be further configured to determine one or more pixel clusters in the video frame, based on a super-pixel clustering technique. The image-processing server 104 may select at least one pixel cluster from the one or more pixel clusters to identify the additional pixels. Further, the image-processing server 104 may recognize the surgical gauze in the video frame based on the selected at least one pixel cluster.

In accordance with an embodiment, the image-processing server 104 may be further configured to adjust one or more image-capture settings of the image-capturing device in real time, based on the recognition of the surgical gauze in the video frame. Examples of the one or more image-capture settings may include, but are not limited to, auto-exposure, auto-focus, auto-white-balance, and/or auto-illumination.

In accordance with an embodiment, the image-processing server 104 may be further configured to display the video frame to a user (such as a physician), via UI of the user terminal 108, while the surgical or diagnostic procedure is performed. The surgical gauze determined in the video frame may be masked or highlighted in the video frame displayed to the user, via the UI. In accordance with an embodiment, the image-processing server 104 may be further configured to generate a notification indicative of the recognition of the surgical gauze. The image-processing server 104 may transmit the notification to the surgical device 102, and/or the user terminal 108. The notification may be presented to the user (such as the physician) by the surgical device 102 and/or the user terminal 108. Examples of the notification may include, but are not limited to, an audio alert, a textual alert, a visual alert, and/or a haptic alert.

Figure 2:
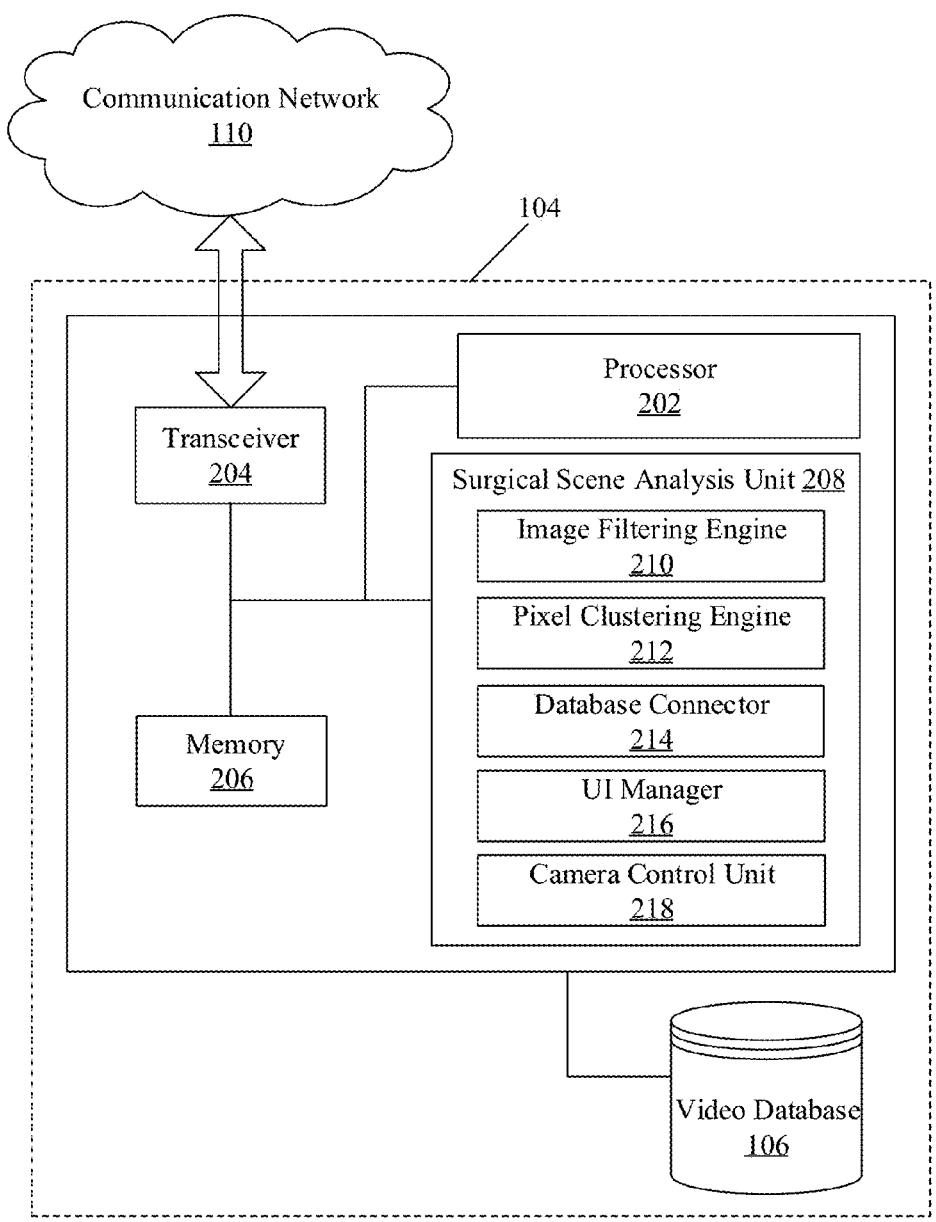
FIG. 2 is a block diagram that illustrates an exemplary image-processing server, in accordance with an embodiment of the disclosure.

FIG. 2 is a block diagram that illustrates an exemplary image-processing server, in accordance with an embodiment of the disclosure. FIG. 2 is explained in conjunction with elements from FIG. 1. With reference to FIG. 2, there is shown the image-processing server 104. The image-processing server 104 may comprise one or more processors (such as a processor 202), one or more transceivers (such as a transceiver 204), a memory 206, and a surgical scene analysis unit 208. The surgical scene analysis unit 208 may include an image-filtering engine 210, a pixel-clustering engine 212, a database connector 214, a UI manager 216, and a camera control unit 218. In accordance with an embodiment, the image-processing server 104 may be communicatively coupled to the video database 106, through the communication network 110, via the transceiver 204. Alternatively, the image-processing server 104 may include the video database 106. For example, the video database 106 may be implemented within the memory 206.

The processor 202 may be communicatively coupled to the transceiver 204, the memory 206, and the surgical scene analysis unit 208. The transceiver 204 may be configured to communicate with the surgical device 102 and the user terminal 108, via the communication network 110.

The processor 202 may comprise suitable logic, circuitry, interfaces, and/or code that may be configured to execute a set of instructions stored in the memory 206. The processor 202 may be implemented, based on a number of processor technologies known in the art. Examples of the processor 202 may be an X86-based processor, a Reduced Instruction Set Computing (RISC) processor, an Application-Specific Integrated Circuit (ASIC) processor, a Complex Instruction Set Computing (CISC) processor, and/or other processors.

The transceiver 204 may comprise suitable logic, circuitry, interfaces, and/or code that may be configured to communicate with the user terminal 108 and/or the surgical device 102, via the communication network 110 (as shown in FIG. 1). The transceiver 204 may implement known technologies to support wired or wireless communication of the image-processing server 104 with the communication network 110. The transceiver 204 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The transceiver 204 may communicate via wireless communication with networks, such as the Internet, an Intranet and/or a wireless network, such as a cellular telephone network, a wireless local area network (LAN) and/or a metropolitan area network (MAN). The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (such as IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

The memory 206 may comprise suitable logic, circuitry, and/or interfaces that may be configured to store a machine code and/or a computer program with at least one code section executable by the processor 202. In accordance with an embodiment, the memory 206 may be further configured to store the one or more video frames captured by the image-capturing device. Examples of implementation of the memory 206 may include, but are not limited to, Random Access Memory (RAM), Read Only Memory (ROM), Hard Disk Drive (HDD), and/or a Secure Digital (SD) card.

The surgical scene analysis unit 208 may comprise suitable logic, circuitry, interfaces, and/or code that may be configured to analyze and process the one or more video frames captured by the image-capturing device. In accordance with an embodiment, the surgical scene analysis unit 208 may be a part of the processor 202. Alternatively, the surgical scene analysis unit 208 may be implemented as a separate processor or circuitry in the image-processing server 104. In accordance with an embodiment, the surgical scene analysis unit 208 and the processor 202 may be implemented as an integrated processor or a cluster of processors that collectively perform the functions of the surgical scene analysis unit 208 and the processor 202. In accordance with another embodiment, the surgical scene analysis unit 208 may be implemented as a computer program code, stored in the memory 206, which on execution by the processor 202 may perform the functions of the surgical scene analysis unit 208.

The image-filtering engine 210 may comprise suitable logic, circuitry, interfaces, and/or code that may be configured to analyze a video frame from the one or more video frames to detect one or more blocks of pixels that correspond to a portion of surgical gauze in the video frame. The image-filtering engine 210 may be configured to determine a set of pixel characteristics, based on color filtering performed on at least a portion of the video frame. The image-filtering engine 210 may be further configured to detect the one or more blocks of pixels that correspond to the portion of the surgical gauze in the video frame, based on the determined set of pixel characteristics.

The pixel clustering engine 212 may comprise suitable logic, circuitry, interfaces, and/or code that may be configured to analyze the video frame to identify additional pixels that correspond to a remaining portion of the surgical gauze and recognize the surgical gauze in the video frame. In accordance with an embodiment, the pixel clustering engine 212 may be configured to identify the additional pixels, based on a plurality of metrics. In accordance with an embodiment, the pixel clustering engine 212 may be further configured to determine one or more pixel clusters in the video frame, based on a super-pixel clustering technique. The identification of the additional pixels may comprise a selection of at least one pixel cluster from the one or more pixel clusters. In accordance with an embodiment, the pixel clustering engine 212 may be further configured to recognize the surgical gauze in the video frame, based on the detection of the one or more blocks that correspond to the portion and the identification of the additional pixels for the remaining portion of the surgical gauze. The recognition of the surgical gauze may be further based on the selected at least one pixel cluster.

The database connector 214 may comprise suitable logic, circuitry, interfaces, and/or code that may be configured to provide the surgical scene analysis unit 208 with access and connectivity to the video database 106. In accordance with an embodiment, the database connector 214 may establish a database session between the surgical scene analysis unit 208 and the video database 106. Examples of one or more communication protocols used to establish the database session may include, but are not limited to, Open Database Connectivity (ODBC)® protocol and Java Database Connectivity (JDBC)® protocol.

The UI manager 216 may comprise suitable logic, circuitry, interfaces, and/or code that may be configured to manage a UI presented on the user terminal 108. In accordance with an embodiment, the UI manager 216 may provide a surgical scene interface to a user (such as a physician) of the user terminal 108. The surgical scene interface may be presented to the user on a display device of the user terminal 108, via the UI of the user terminal 108. In accordance with an embodiment, the surgical scene interface may be configured to display the one or more video frames to the user. The surgical gauze recognized in the video frame may be masked or highlighted in the respective video frame from the one or more video frames displayed to the user, via the surgical scene interface.

The camera control unit 218 may comprise suitable logic, circuitry, interfaces, and/or code that may be configured to communicate with the image-capturing device to adjust one or more image-capture settings of the image-capturing device. In accordance with an embodiment, the camera control unit 218 may be configured to determine such values of the one or more image-capture settings, which may be suitable or optimal to capture the one or more video frames, based on the recognition of the surgical gauze. Thereafter, the camera control unit 218 may be configured to transmit the determined values of the one or more image-capture settings to the image-capturing device, via the transceiver 204. The image-capturing device may adjust its image-capturing settings, based on the corresponding values that are sent by the camera control unit 218. Examples of the one or more image-capture settings may include, but are not limited to, auto-exposure, auto-focus, auto-white-balance, or auto-illumination.

In operation, a physician may perform a surgical or diagnostic procedure on anatomical region of a patient, by use of the surgical device 102 and one or more surgical instruments. Examples of the one or more surgical instruments may include, but are not limited to, endoscopic catheters, surgical forceps, surgical incision instruments, and/or surgical gauze. Examples of the surgical or diagnostic procedure may include, but are not limited to, a minimally invasive surgery/diagnosis procedure, a minimal incision surgery/diagnosis procedure, a laparoscopic procedure, and/or an endoscopic procedure.

In accordance with an embodiment, the surgical or diagnostic procedure may be automated and performed by a surgical robot, without any supervision or direction from the physician. In accordance with an embodiment, the surgical or diagnostic procedure may be semi-automated and performed by the surgical robot, with one or more input signals and/or commands from the physician. In accordance with an embodiment, the image-capturing device (not shown in FIG. 1) may be communicatively coupled to (or included within) the surgical device 102. The image-capturing device may capture video frames of the anatomical region in real time, while the surgical or diagnostic procedure is performed on the anatomical region. Thereafter, the surgical device 102 (or the image-capturing device itself) may transmit the captured video frames to the image-processing server 104, via the communication network 110.

The transceiver 204, in the image-processing server 104, may be configured to receive the video frames from the surgical device 102, via the communication network 110. In accordance with an embodiment, the video frames may be received as real-time streamed media content by use of a communication protocol, such as a real-time transport protocol (RTP), and/or a real-time streaming protocol (RTSP). The database connector 214 may be configured to establish a database session with the video database 106 and store the received video frames in the video database 106. Further, the video frames may also be stored in the memory 206.

The image-filtering engine 210 may be configured to analyze the video frames. In accordance with an embodiment, the video frames may be analyzed in a batch mode (offline processing), when a predetermined number of video frames are received from the surgical device 102. In accordance with an embodiment, the video frames may be analyzed on a real-time basis (online processing), upon receipt of each new video frame. The image-filtering engine 210 may retrieve the video frames from the memory 206 or the video database 106 for analysis of the video frames.

In accordance with an embodiment, the image-filtering engine 210 may divide each video frame into image blocks (interchangeably referred to hereafter as "blocks of pixels" and/or "blocks") for analysis. The image-filtering engine 210 may be configured to perform color filtering on at least a portion (that may include one or more such image blocks) of the video frame to determine a set of pixel characteristics for at least a portion of the video frame. Examples of the set of pixel characteristics may include, but are not limited to, an edge feature, a shape feature, a texture feature, a size feature, a color feature, an intensity feature, or a density feature. The image-filtering engine 210 may be configured to apply one or more color constraints on the pixels in the video frame. In accordance with an embodiment, the color of the surgical gauze in the video frame may be one of, but not limited to, red (in case of blood-soaked surgical gauze), white (in case of blood-free surgical gauze), or blue (in case of radioactive-striped surgical gauze). In accordance with an embodiment, the image-filtering engine 210 may apply the one or more color constraints based on one or more conditions, such as "Condition 1", "Condition 2", "Condition 3", and "Condition 4", as follows:

| | |
|---|---|
| $\|g-b\|<25$ and $r \geq 88$ | Condition 1: |
| $I_{gray} \geq 150$ and $I_{opp2} \leq 33$ | Condition 2: |
| $b+6 \geq g$ and $I_{opp2} > 33$ | Condition 3: |
| $b \geq r+5$ and $I_{gray} \geq 150$ | Condition 4: | where r, g, b represent red, green, and blue color components of a pixel;
$I_{gray}$ represents a grey-scale intensity of the pixel; and
$I_{opp2}$ represents an opp2 color intensity of the pixel.

In accordance with an embodiment, the image-filtering engine 210 may check the condition, "Condition 1", to identify regions that may encompass a white (blood-free) surgical gauze or a red (blood-soaked) surgical gauze. Pixels in such regions may have a small absolute difference (such as "25 or less") between their green and blue color components. Further, the red color component of these pixels may have a moderate value (such as "88 or more").

In accordance with an embodiment, the image-filtering engine 210 may check the condition, "Condition 2", to identify regions that may encompass a white (blood-free) surgical gauze but exclude silver-colored surgical tools. The "Condition 2" may be based on an assumption that such regions may include pixels that have a high grey-scale intensity and low opp2 color intensity.

In accordance with an embodiment, the image-filtering engine 210 may check the condition, "Condition 3", to identify regions that may encompass a red (blood-soaked) surgical gauze, but exclude yellowish tissues. The blue color component of each pixel in such regions may be marginally greater than the green color component of the respective pixels.

In accordance with an embodiment, the image-filtering engine 210 may check the condition, "Condition 4", to identify regions that may encompass a blue (radioactive-striped) surgical gauze. Pixels in such regions may have higher blue color component values as compared to their red color component values. Further, the pixels in such regions may have higher grey-scale pixel intensities (such as "150 or more").

In accordance with an embodiment, the image-filtering engine 210 may detect regions of interest in the video frame that may correspond to a white (blood-free) surgical gauze, based on the conditions, "Condition 1" and "Condition 2". Further, the image-filtering engine 210 may detect regions of interest in the video frame that may correspond to a red (blood-soaked) surgical gauze based on the conditions, "Condition 1" and "Condition 3". In addition, the image-filtering engine 210 may detect regions of interest in the video frame that may correspond to a blue (radioactive-striped) surgical gauze based on the condition, "Condition 4". Hereinafter, the term "region of interest" is used to refer to those regions that are identified by the image-filtering engine 210 in the video frame based on the various image filtering conditions mentioned above (such as, but not limited to, "Condition 1", "Condition 2", "Condition 3", and "Condition 4").

Further, the image-filtering engine 210 may be configured to perform edge filtering to detect edge pixels in the video frame. In accordance with an embodiment, the edge filtering may be performed on the video frame by use of a Sobel edge filter, known in the art. The image-filtering engine 210 may detect a pixel to be an edge pixel based on the following condition:

$I_{sobel} \geq 7182$                  Condition 5:

where "$I_{sobel}$" represents Sobel energy of a pixel.

Thus, the image-filtering engine 210 may check the condition, "Condition 5", to determine whether the Sobel energy of a pixel is greater than a threshold (such as "7182"). If the Sobel energy of a particular pixel is greater than the threshold, the image-filtering engine 210 may detect the pixel as an edge pixel. A person having ordinary skill in the art will understand that surgical gauze may have stripes. The detection of the edge pixels in the video frame may enable the identification of stripes in the video frame, and hence may enable the image-filtering engine 212 to identify those regions of interest that may encompass surgical gauze. Further, a region that corresponds to a blood-soaked surgical gauze may have more edges that a region that corresponds to a tissue in the video frame. Hence, the detection of the edge pixels in the video frame may enable the image-filtering engine 210 to accurately distinguish between blood-soaked surgical gauze and tissues in the video frame.

In accordance with an embodiment, the image-filtering engine 210 may be further configured to perform a density analysis of edge pixels in the detected regions of interest in the video frame. Based on the density analysis, the image-filtering engine 210 may determine a density of stripes in each image block within the detected regions of interest in the video frame. In accordance with an embodiment, the density of stripes in an image block may correspond to a ratio of the number of edge pixels in the image block to the total number of pixels in the image block. The image-filtering engine 210 may generate a confidence map to detect a portion of the surgical gauze in the video frame, based on the density of stripes in each image block in the regions of interest in the video frame. In accordance with an embodiment, the image-filtering engine 210 may generate the confidence map based on the following condition:

$d_{\Omega} \geq 0.3$                  Condition 6:

where "$d_{\Omega}$" represents a density of stripes in an image block in a region of interest of the video frame.

Thus, the image-filtering engine 210 may check the condition, "Condition 6", to identify image blocks in the detected regions of interest of the video frame that have a high density of stripes. Pixels in such image blocks may have a high likelihood that they may correspond to the surgical gauze. Thus, the image-filtering engine 210 may include the pixels of such image blocks in the confidence map. In accordance with an embodiment, the image-filtering engine 210 may generate the confidence map by assignment of likelihood values to pixels in each such image block, based on the density of stripes in the respective image blocks.

In accordance with an embodiment, the image-filtering engine 210 may be further configured to detect one or more blocks of pixels that may correspond to the portion of the surgical gauze in the video frame, based on the determined set of pixel characteristics. In accordance with an embodiment, the detection of such blocks of pixels may be based on a connected component analysis of at least a portion (that may include one or more image blocks) of the video frame.

The image-filtering engine 210 may perform a thresholding operation on the regions of interest detected in the video frame, based on the confidence map. For instance, the image-filtering engine 210 may perform the thresholding operation by selection of those pixels in the regions of interest that are assigned a likelihood value (within the confidence map) of greater than a predetermined threshold (such as "0.5").

Thereafter, the image-filtering engine 210 may link connected components in the regions of interest of the video frame, based on the confidence map. In accordance with an embodiment, the image-filtering engine 210 may link the connected components such that each connected component may include at least a predetermined number (such as five or more) of consecutive image blocks of the video frame. The consecutive image blocks may satisfy conditions of the thresholding operation. The image-filtering engine 210 may then identify image blocks that lie within the linked, connected components as the detected one or more blocks of pixels that may correspond to the portion of the surgical gauze in the video frame. An exemplary flow diagram that illustrates a method for detection of one or more image blocks that correspond to surgical gauze in a video frame is explained in FIG. 4.

In accordance with an embodiment, the pixel clustering engine 212 may be configured to identify additional pixels that may correspond to a remaining portion of the surgical gauze in the video frame based on a plurality of metrics. In accordance with an embodiment, the plurality of metrics may comprise at least a spatial metric and a spectral metric. The spatial metric may correspond to a geometric distance between coordinates of two pixels in the video frame. In accordance with an embodiment, the coordinates of the pixels of the video frame may be normalized based on dimensions of the video frame. For instance, the normalized coordinates of a pixel may be represented by equation (1), as follows:

$$\text{Normalized Pixel Coordinates} = \left( \frac{x}{\max(x)}, \frac{y}{\max(y)} \right) \quad (1)$$

where "max(x)" represents the maximum x-coordinates of pixels in the video frame; and "max(y)" represents the maximum y-coordinates of pixels in the video frame.

Further, the spectral metric may correspond to a lighting-invariant color metric, which may be determined based on a cosine distance between color components of two pixels in the video frame. In accordance with an embodiment, each color component of the pixels may be normalized based on a root of the sum of squared values of the color components of pixels. For instance, the normalized color components of a pixel may be represented by equation (2), as follows:

$$\text{Normalized Color Components} = \left( \frac{R}{(R^2 + G^2 + B^2)^{1/2}}, \frac{G}{(R^2 + G^2 + B^2)^{1/2}}, \frac{B}{(R^2 + G^2 + B^2)^{1/2}} \right) \quad (2)$$

where "R", "G", and "B" represent the red, green, and blue color components of the pixel.

In accordance with an embodiment, the pixel clustering engine 212 may be configured to determine a Euclidean distance between each pair of pixels that lie in the regions of interest. As discussed above, these regions of interest in the video frame may be identified based on the one or more color constraints, such as the conditions, "Condition 1", "Condition 2", "Condition 3", and "Condition 4". In accordance with an embodiment, the pixel clustering engine 212 may determine the Euclidean distance based on the spatial metric, the spectral metric, and a weighting parameter. The Euclidean distance may be represented by equation (3), as follows:

$$d=|(\alpha R, \alpha G, \alpha B, X, Y)| \qquad (3)$$

where "d" represents the Euclidean distance between a pair of pixels;
"R", "G", and "B" represent differences between respective normalized red, green, and blue color components of the pair of pixels;
"X" and "Y" represent differences between respective normalized x and y pixel coordinates of the pair of pixels; and
"α" represents the weighting parameter (which may be user-specified or configured by the pixel clustering engine 212).

In accordance with an embodiment, the pixel clustering engine 212 may be further configured to cluster pixels of the regions of interest in the video frame to identify the additional pixels that may correspond to the surgical gauze. In accordance with an embodiment, the pixel clustering engine 212 may cluster the pixels in the identified regions of interest by use of a k-means clustering technique based on the Euclidean distance between each pair of such pixels. Notwithstanding, the disclosure may not be so limited and the pixel clustering engine 212 may combine the spatial metric, the spectral metric, and a weighting parameter to determine the distance between two pixels in the video frame using other mathematical functions known in the art, without deviation from the scope of the disclosure.

In accordance with an embodiment, the pixel clustering engine 212 may be configured to determine one or more pixel clusters in the video frame, based on a super-pixel clustering technique. The pixel clustering engine 212 may combine a predetermined number of pixels in the regions of interest to generate one or more super-pixels. The pixel clustering engine 212 may determine the set of pixel characteristics for each of the one or more super-pixels, based on the set of pixel characteristics of pixels that are encompassed in each respective super-pixel. For example, the pixel clustering engine 212 may determine coordinates of a super-pixel, based on coordinates of centroid of a region that encompasses the pixels of the super-pixel.

Further, the pixel clustering engine 212 may determine color components of a super-pixel, based on color components of the pixels of the super-pixel. For instance, the pixel clustering engine 212 may perform an averaging operation on each color component of the individual pixels of the super-pixel to determine the values of the respective color components of the super-pixel. Examples of the averaging operation may include, mean, rolling average, weighted average, median, mode, and/or any other applied mathematical or statistical aggregation techniques. In accordance with an embodiment, the pixel clustering engine 212 may determine the Euclidean distance between each pair of super-pixels that may be generated from the regions of interest in the video frame. Based on the determined Euclidean distances, the pixel clustering engine 212 may determine the one or more pixel clusters in the video frame.

In accordance with an embodiment, the pixel clustering engine 212 may be further configured to select at least one pixel cluster from the one or more pixel clusters determined in the video frame. The selection of the at least one pixel cluster may be based on a size of the at least one pixel cluster. For instance, the pixel clustering engine 212 may select those pixel clusters from the one or more pixel clusters that are larger than a threshold size. The pixel clustering engine 212 may identify pixels encompassed within the selected at least one pixel cluster as the additional pixels that may correspond to the remaining portion of the surgical gauze.

Further, the pixel clustering engine 212 may be configured to overlay the one or more super-pixels within the regions of interest over the one or more blocks detected as the portion of the surgical gauze in the video frame. The pixel clustering engine 212 may then validate whether the one or more blocks encompass the surgical gauze, based on an extent of coverage of the one or more super-pixels by these one or more blocks. For instance, the pixel clustering engine 212 may determine the number of super-pixels that are encompassed by the one or more blocks. If the number of super-pixels encompassed by the one or more blocks is more than a predetermined threshold (such as "30 percent of the total number of super-pixels"), the pixel clustering engine 212 may validate the one or more blocks as the portion of the surgical gauze in the video frame.

In accordance with an embodiment, the pixel clustering engine 212 may be configured to recognize the surgical gauze in the video frame, based on the detection of the one or more blocks of pixels that may correspond to the portion of the surgical gauze and the identification of the additional pixels that may correspond to the remaining portion of the surgical gauze. The pixel clustering engine 212 may combine the selected at least one pixel cluster with the validated one or more blocks of the portion of the surgical gauze to recognize the surgical gauze. An exemplary flow diagram that illustrates a method for recognition of surgical gauze in a video frame is explained in FIG. 5.

A person having ordinary skill in the art will understand that the values of the various predetermined thresholds are exemplary values. The values of the predetermined thresholds may vary, based on implementation, hardware and/or software configuration, and user requirements, without deviation from the scope of the disclosure.

In accordance with an embodiment, the UI manager 216 may be configured to present a surgical scene interface to a user, such as a physician, of the user terminal 108. The surgical scene interface may be presented to the user on a display device of the user terminal 108, via a UI of the user terminal 108. In accordance with an embodiment, the surgical scene interface may be configured to display the one or more video frames of the surgical or diagnostic procedure to the user. The surgical gauze recognized in a particular video frame may be masked or highlighted when that video frame is displayed to the user, via the surgical scene interface. An exemplary UI that may be presented to the user to display the surgical scene interface is explained in FIG. 6.

In accordance with an embodiment, the UI manager 216 may be further configured to generate a notification that signals the recognition of the surgical gauze in a particular video frame. The UI manager 216 may send the generated notification to the user terminal 108. The notification may be presented to the user, via the UI of the user terminal 108. In case of real-time or online analysis of the one or more video frames for recognition of the surgical gauze, the UI manager 216 may also transmit the generated notification to surgical device 102, via the transceiver 204. Examples of the notification may include, but are not limited to, an audio alert, a textual alert, a visual alert, and/or a haptic feedback.

In accordance with an embodiment, the camera control unit 218 may be configured to determine optimal values for one or more image-capture settings of the image-capturing device, based on the recognition of the surgical gauze in the video frame. Examples of the one or more image-capture settings may include, but are not limited to, auto-exposure, auto-focus, auto-white-balance, or auto-illumination. In accordance with an embodiment, the optimal values of the one or more image-capture settings may be determined, based on one or more conditions, such as a size of a region recognized as the surgical gauze in the video frame, an average intensity of pixels in such region, and/or one or more features of such a region. In an embodiment, the determination of the optimal values may be also based on user-specified criteria. The camera control unit 218 may be configured to transmit the optimal values of the one or more image-capture settings to the image-capturing device, via the transceiver 204. The one or more image-capture settings of the image-capturing device may be adjusted based on the respective optimal values sent by the camera control unit 218.

In accordance with an embodiment, the UI manager 216 may present the optimal values of the one or more image-capture settings to the user, via the UI of the user terminal 108. The UI manager 216 may enable the user to confirm or adjust the optimal values, via the UI of the user terminal 108. The UI manager 216 may receive a user input indicative of a confirmation or an adjustment of the optimal values from the user terminal 108, via the transceiver 204. Thereafter, the camera control unit 218 may update the optimal values, based on the user input, and transmit the updated optimal values to the image-capturing device, via the transceiver 204. The one or more image-capture settings of the image-capturing device may be adjusted based on the updated optimal values received from the camera control unit 218.

Figure 3:
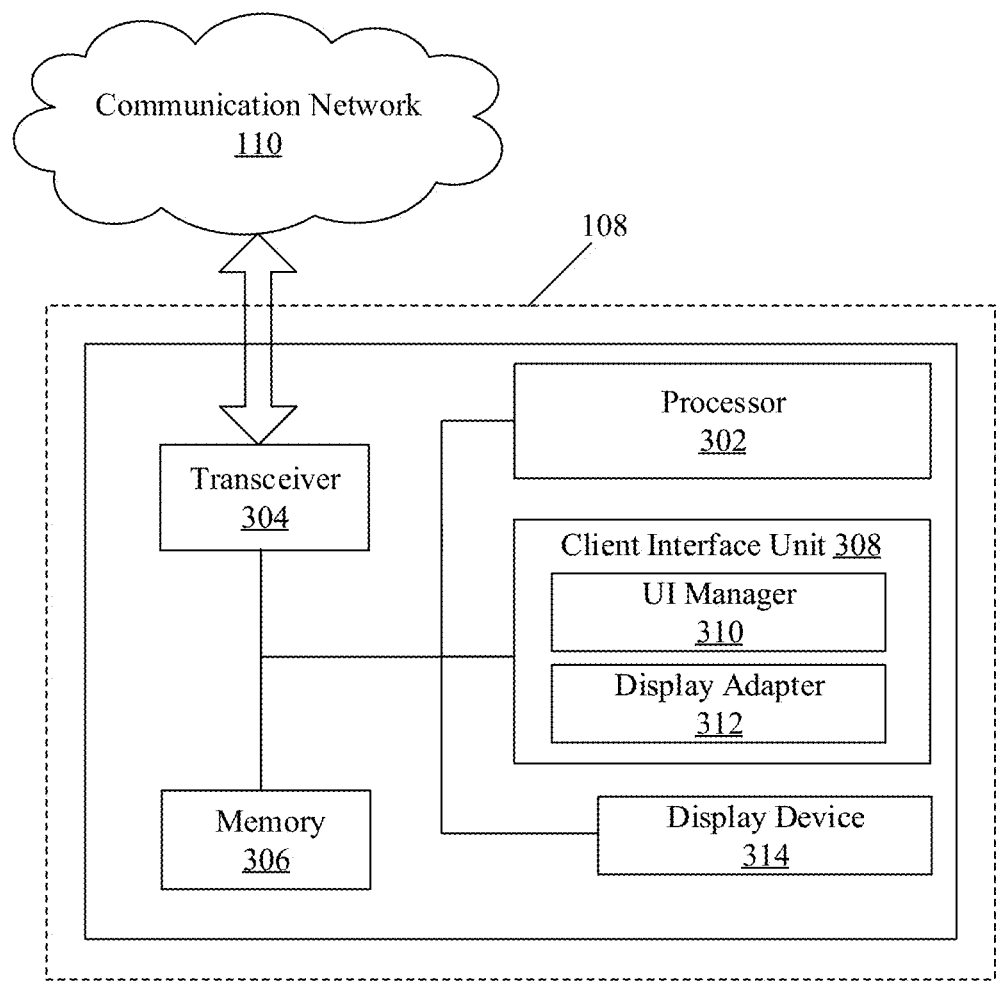
FIG. 3 is a block diagram that illustrates an exemplary user terminal, in accordance with an embodiment of the disclosure.

FIG. 3 is a block diagram that illustrates an exemplary user terminal, in accordance with an embodiment of the disclosure. FIG. 3 is explained in conjunction with elements from FIG. 1. With reference to FIG. 3, there is shown the user terminal 108. The user terminal 108 may comprise one or more processors (such as a processor 302), one or more transceivers (such as a transceiver 304), a memory 306, a client interface unit 308, and a display device 314. The client interface unit 308 may include a UI manager 310 and a display adapter 312. The processor 302 may be communicatively coupled to the transceiver 304, the memory 306, the client interface unit 308, and the display device 314. The transceiver 304 may be configured to communicate with the image-processing server 104 and/or the surgical device 102, via the communication network 110.

The processor 302 may comprise suitable logic, circuitry, interfaces, and/or code that may be configured to execute a set of instructions stored in the memory 306. The processor 302 may be implemented, based on a number of processor technologies known in the art. Examples of the processor 302 may be an X86-based processor, a Reduced Instruction Set Computing (RISC) processor, an Application-Specific Integrated Circuit (ASIC) processor, a Complex Instruction Set Computing (CISC) processor, and/or other processors.

The transceiver 304 may comprise suitable logic, circuitry, interfaces, and/or code that may be configured to communicate with the image-processing server 104 and/or the surgical device 102, via the communication network 110 (as shown in FIG. 1). The transceiver 304 may implement known technologies to support wired or wireless communication of the user terminal 108 with the communication network 110. The transceiver 304 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The transceiver 304 may communicate via wireless communication with networks, such as the Internet, an Intranet and/or a wireless network, such as a cellular telephone network, a wireless local area network (LAN) and/or a metropolitan area network (MAN). The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (such as IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

The memory 306 may comprise suitable logic, circuitry, and/or interfaces that may be configured to store a machine code and/or a computer program with at least one code section executable by the processor 302. Examples of implementation of the memory 306 may include, but are not limited to, Random Access Memory (RAM), Read Only Memory (ROM), Hard Disk Drive (HDD), and/or a Secure Digital (SD) card.

The client interface unit 308 may comprise suitable logic, circuitry, interfaces, and/or code that may be configured to render and manage one or more UIs presented on the user terminal 108. In accordance with an embodiment, the client interface unit 308 may be a part of the processor 302. Alternatively, the client interface unit 308 may be implemented as a separate processor or circuitry in the user terminal 108. For example, the client interface unit 308 may be implemented as a dedicated graphics processor or chipset, communicatively coupled to the processor 302. In accordance with an embodiment, the client interface unit 308 and the processor 302 may be implemented as an integrated processor, or a cluster of processors, which perform the functions of the client interface unit 308 and the processor 302. In accordance with another embodiment, the client interface unit 308 may be implemented as a computer program code, stored in the memory 306, which on execution by the processor 302, may perform the functions of the client interface unit 308.

The UI manager 310 may comprise suitable logic, circuitry, interfaces, and/or code that may be configured to manage the UI of the user terminal 108. In accordance with an embodiment, the UI manager 310 may be further configured to receive and process user input received via the UI of the user terminal 108, via an input device (not shown in FIG. 3) of the user terminal 108. In accordance with an embodiment, the input device may be communicatively coupled to (or included within) the user terminal 108. Examples of the input device may include, but are not limited to, a keyboard, a mouse, a joy stick, a track pad, a voice-enabled input device, a touch-enabled input device, and/or a gesture-enabled input device.

In accordance with an embodiment, the UI manager 310 may be further configured to communicate with the UI manager 216, of the image-processing server 104, via the transceiver 304. Such communication may facilitate receipt of information that corresponds to the surgical scene interface. Thereafter, the UI manager 310 may present the surgical scene interface via the UI of the user terminal 108.

The display adapter 312 may comprise suitable logic, circuitry, interfaces, and/or code that may be configured to interface the UI manager 310 with the display device 314. In accordance with an embodiment, the display adapter 312 may perform an adjustment of rendering and display properties of the UI of the user terminal 108, based on display configurations of the display device 314. Examples of one or more techniques that may be employed to perform the display adjustment may include, but are not limited to, image enhancement, image stabilization, contrast adjustment, brightness adjustment, resolution adjustment, and/or skew/rotation adjustment.

The display device 314 may comprise suitable logic, circuitry, interfaces, and/or code that may be configured to render the UI. In accordance with an embodiment, the display device 314 may be implemented as a part of the user terminal 108. In another embodiment, the display device 314 may be communicatively coupled to the user terminal 108. The display device 314 may be realized through several known technologies, such as Cathode Ray Tube (CRT) based display, Liquid Crystal Display (LCD), Light Emitting Diode (LED) based display, Organic LED display technology, Retina display technology, and/or the like. In addition, in accordance with an embodiment, the display device 314 may receive input from the user. In such a scenario, the display device 314 may be a touch screen that enables the user to provide the input. In accordance with an embodiment, the touch screen may correspond to at least one of a resistive touch screen, a capacitive touch screen, or a thermal touch screen. In accordance with an embodiment, the display device 314 may receive the input through a virtual keypad, a stylus, a gesture-based input, and/or a touch-based input. In such a case, the input device may be integrated within the display device 314. In addition, in accordance with an embodiment, the user terminal 108 may include a secondary input device apart from a touch-screen-based display device 314.

In operation, the transceiver 304 of the user terminal 108 may receive information that may correspond to the surgical scene interface from the UI manager 216, of the image-processing server 104, via the communication network 110. Thereafter, in accordance with an embodiment, the UI manager 310 of the user terminal 108 may present the surgical scene interface to the user, via the UI of the user terminal 108. In accordance with an embodiment, the surgical scene interface may present the one or more video frames of the surgical or diagnostic procedure to the user. In accordance with an embodiment, the surgical gauze recognized in a particular video frame may be masked or highlighted when the video frame is displayed to the user. An example of the surgical scene interface is explained in more detail in FIG. 6.

In accordance with an embodiment, the one or more video frames presented by the surgical scene interface may be real-time video footage captured by the image-capturing device while the surgical or diagnostic procedure is performed. In such a case, the image-processing server 104 may analyze the one or more video frames on a real-time basis (online processing) to recognize the surgical gauze in at least one video frame. The surgical gauze recognized in a particular video frame may be simultaneously presented to the user as a masked or highlighted region within the video frame, via the surgical scene interface.

In accordance with an embodiment, the surgical scene interface may be further configured to present a notification to the user to indicate the recognition of the surgical gauze. Examples of the notification may include, but are not limited to, an audio alert, a textual alert, a visual alert, and/or a haptic alert. The user (such as the physician) may be prompted to take an appropriate action based on the notification. For instance, the surgical scene interface may prompt the user to adjust the one or more image-capture settings of the image-capturing device. In accordance with an embodiment, the camera control unit 218 of the image-processing server 104 may be configured to determine optimal values for the one or more image-capture settings, based on the recognition of the surgical gauze. The surgical scene interface may present these optimal values to the user as suggested values for the one or more image-capture settings. The user may adjust the one or more image-capture settings of the image-capturing device, based on the suggested values presented to the user. In addition to adjustment of the one or more image-capture settings of the image-capturing device, the user (such as the physician) may reposition/remove the surgical gauze within/from the body cavity around the anatomical region of the patient.

Figure 4:
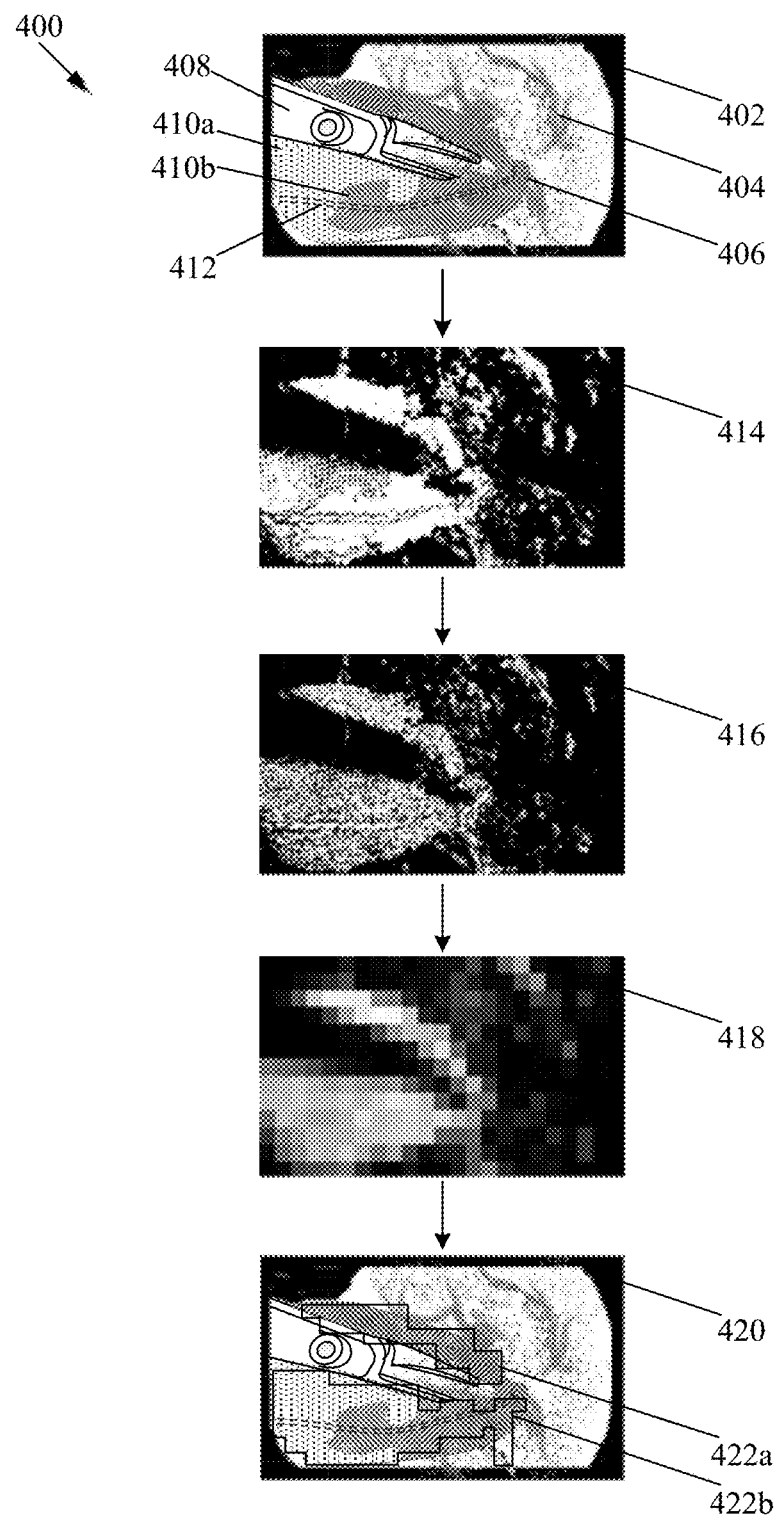
FIG. 4 illustrates an exemplary flow diagram that illustrates a method to detect one or more image blocks that correspond to surgical gauze in a video frame, in accordance with an embodiment of the disclosure.

FIG. 4 illustrates an exemplary flow diagram that illustrates a method to detect one or more image blocks that correspond to surgical gauze in a video frame, in accordance with an embodiment of the disclosure. FIG. 4 has been described in conjunction with elements from FIGS. 1 and 2. With reference to FIG. 4, there is shown a flow diagram 400. The flow diagram 400 comprises an input video frame 402, an anatomical region 404, surgical gauze 406, a surgical instrument 408, a blood-free region 410a, a blood-soaked region 410b, a radioactive-stripe 412, a color-filtered video frame 414, an edge-filtered video frame 416, a confidence-mapped video frame 418, an output video frame 420, a first portion 422a, and a second portion 422b.

As shown in the flow diagram 400, the input video frame 402 illustrates a snapshot of a video frame from the one or more video frames captured by the image-capturing device. The input video frame 402 depicts the anatomical region 404, on which a surgical or diagnostic procedure is performed by use of the surgical instrument 408. The input video frame 402 also depicts the surgical gauze 406 that may be used during the surgical or diagnostic procedure. The surgical gauze 406 may include the blood-free region 410a and the blood-soaked region 410b. The blood-free region 410a in the surgical gauze 406 may appear white in color, while the blood-soaked region 410b in the surgical gauze 406 may appear red in color. Further, the surgical gauze 406 may include the radioactive-stripe 414 that may appear blue in color.

In accordance with an embodiment, the image-filtering engine 210 of the image-processing server 104 may be configured to analyze the input video frame 402 to determine the set of pixel characteristics of at least a portion of the input video frame 402. The set of pixel characteristics may include, but are not limited to, an edge feature, a shape feature, a texture feature, a size feature, a color feature, an intensity feature, or a density feature. The set of pixel characteristics may be determined based on color filtering performed on at least a portion of the input video frame 402. In accordance with an embodiment, the image-filtering engine 210 may perform the color filtering based on one or more conditions, such as the conditions, "Condition 1", "Condition 2", "Condition 3", and "Condition 4", as specified in FIG. 2. The color-filtered video frame 414 illustrates a resultant video frame that may be obtained from the input video frame 402, based on the color filtering of the input video frame 402. The color-filtered video frame 414 may include regions of interest that may correspond to the surgical gauze 406 in the input video frame 402.

In accordance with an embodiment, the image-filtering engine 210 may be configured to detect edge pixels within the regions of interest in the color filtered video frame 414. The image-filtering engine 210 may detect the edge pixels by use of a Sobel edge filter based on the condition, "Condition 5", as specified in FIG. 2. The edge-filtered video frame 416 illustrates a resultant video frame that may be obtained based on the detection of the edge pixels in the color-filtered video frame 414.

In accordance with an embodiment, the image-filtering engine 210 may be configured to perform a density analysis of the edge pixels detected in the edge-filtered video frame 416. The image-filtering engine 210 may determine a density of stripes in each image block of the edge-filtered video frame 416, based on the density analysis. Thereafter, the image-filtering engine 210 may generate a confidence map to detect one or more portions of the surgical gauze 406 in the input video frame 402. The confidence map may be built by using the condition, "Condition 6" (as specified in FIG. 2) based on the density of stripes in each image block of the edge-filtered video frame 416. The confidence-mapped video frame 418 illustrates a resultant video frame that may be obtained when the confidence map is overlaid on the edge-filtered video frame 416.

In accordance with an embodiment, the image-filtering engine 210 may be further configured to detect one or more blocks of pixels that may correspond to a portion of the surgical gauze 406, in the input video frame 402, based on the determined set of pixel characteristics. The image-filtering engine 210 may perform a connected-component analysis of at least a portion (that may include one or more image blocks) in the input video frame 402. The image-filtering engine 210 may perform a thresholding operation on the regions of interest of the input video frame 402 (as identified in the edge-filtered video frame 416). The thresholding operation may be performed based on the confidence map represented in the confidence-mapped video frame 418.

Thereafter, the image-filtering engine 210 may link connected components in the regions of interest of the input video frame 402, based on the confidence map. For instance, each connected component may include at least a predetermined number (such as "five or more") of consecutive image blocks that may satisfy one or more conditions of the thresholding operation. The image-filtering engine 210 may then identify those image blocks that lie within the linked, connected components as the detected one or more blocks of pixels that may correspond to the portions of the surgical gauze 406 in the input video frame 402. For instance, the image-filtering engine 210 may identify the first portion 422*a* and the second portion 422*b*, as the portions of the surgical gauze 406 in the input video frame 402.

The output video frame 420 illustrates a resultant video frame that may be obtained when the first portion 422*a* and the second portion 422*b* are identified and masked in the input video frame 402. As is evident from FIG. 4, the first portion 422*a* and the second portion 422*b* may not encompass the entire surgical gauze 406. The pixel clustering engine 212 may be configured to identify additional pixels in the output video frame 420 that may correspond to the surgical gauze. Based on the identification of the first portion 422*a*, the second portion 422*b*, and the additional pixels, the surgical gauze 406 may be recognized within the input video frame 402.

Figure 5:
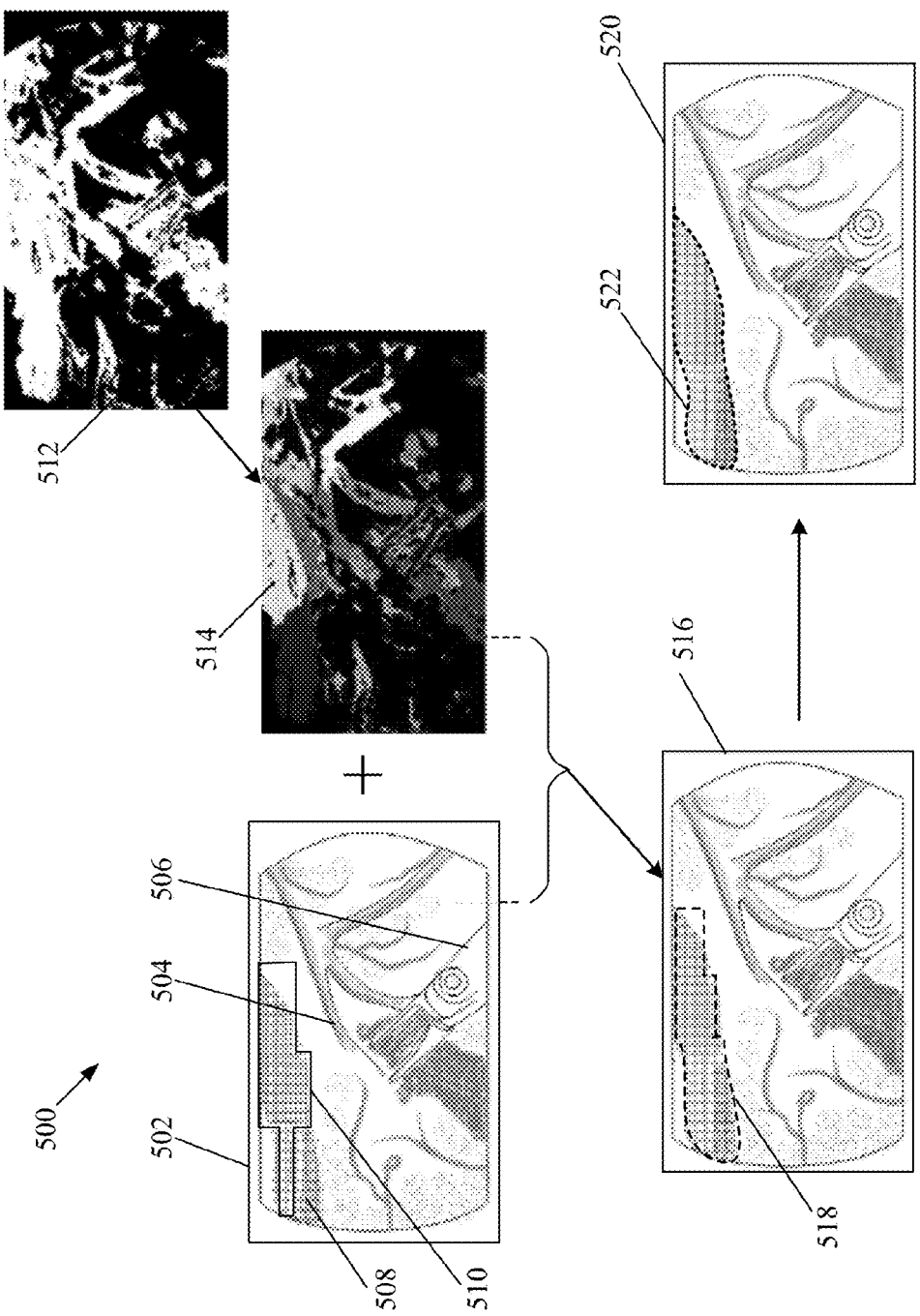
FIG. 5 illustrates another exemplary flow diagram that illustrates a method to recognize surgical gauze in a video frame, in accordance with an embodiment of the disclosure.

FIG. 5 illustrates an exemplary flow diagram that illustrates a method to recognize surgical gauze in a video frame, in accordance with an embodiment of the disclosure. FIG. 5 has been described in conjunction with elements from FIGS. 1 and 2. With reference to FIG. 5, there is shown a flow diagram 500. The flow diagram 500 comprises a pre-processed video frame 502, an anatomical region 504, a surgical instrument 506, surgical gauze 508, a pre-identified portion 510, a color/edge-filtered video frame 512, a pixel-clustered video frame 514, a post-processed video frame 516, a first boundary 518, an output video frame 520, and a second boundary 522.

As shown in the flow diagram 500, the pre-processed video frame 502 illustrates a snapshot of a resultant video frame that may be obtained based on a preliminary analysis of an input video frame (not shown in FIG. 5), captured by the image-capturing device. The image-filtering engine 210 may perform the preliminary analysis of the input video frame to detect a portion of surgical gauze in the input video frame (in a manner similar to that illustrated in the flow diagram 400 of FIG. 4).

The image-filtering engine 210 may then mask the detected portion of the surgical gauze in the input video frame, to generate the pre-processed video frame 502. The pre-processed video frame 502 depicts the anatomical region 504, on which a surgical or diagnostic procedure is performed by use of the surgical instrument 506. The pre-processed video frame 502 also depicts the surgical gauze 508 that may be used during the surgical or diagnostic procedure. In addition, the pre-processed video frame 502 depicts the pre-identified portion 510 as a portion of the surgical gauze 508 in the input video frame that may be identified by the image-filtering engine 210, based on the preliminary analysis of the input video frame.

In accordance with an embodiment, the image-filtering engine 210 may generate a color-filtered video frame (not shown in FIG. 5) by color filtering of the input video frame based on one or more conditions, such as "Condition 1", "Condition 2", "Condition 3", and "Condition 4", as specified in FIG. 2. Further, the image-filtering engine 210 may identify edge pixels in the color-filtered video frame (not shown in FIG. 5). The image-filtering engine 210 may use the condition, "Condition 5" (as specified in FIG. 2), to identify the edge pixels. Thereafter, based on the color filtering of the input video frame and the identification of the edge pixels in the color-filtered input video frame, the image-filtering engine 210 may generate the color/edge-filtered video frame 512. The color/edge-filtered video frame 512 may include one or more regions of interest of the video frame that may include other portions of the surgical gauze 508.

In accordance with an embodiment, the pixel clustering engine 212 may be configured to identify one or more pixel clusters in the color/edge-filtered video frame 512, by use of a super-pixel clustering technique. The pixel clustering engine 212 may perform the super-pixel clustering based on a plurality of metrics, such as a spatial metric and a spectral metric. For instance, the pixel clustering engine 212 may determine a Euclidean distance between each pair of pixels in the regions of interest in the color/edge-filtered video frame 512. The Euclidean distance may be based on the spatial metric, the spectral metric, and a weighting parameter. The pixel-clustered video frame 514 illustrates a resultant video frame that may be generated from the color/edge-filtered video frame based on the super-pixel clustering. The pixel-clustered video frame 514 may include the one or more pixel clusters that may be identified from the color/edge-filtered video frame 512.

In accordance with an embodiment, the pixel clustering engine 212 may overlay the pre-processed video frame 502, over the pixel-clustered video frame 514, to obtain the post-processed video frame 516. The pixel clustering engine 212 may determine the extent of overlap of the one or more clusters with the pre-identified portion 510. The pixel clustering engine 212 may determine a first set of additional pixels that may correspond to the surgical gauze 508, based on the extent of overlap of the one or more clusters. Thereafter, the pixel clustering engine 212 may combine the first set of additional pixels with the pre-identified portion 510, to generate the first boundary 518, which may encompass the surgical gauze 508.

In accordance with an embodiment, the pixel clustering engine 212 may select at least one cluster from the one or more clusters, based on at least the size of each of the one or more clusters. Thereafter, the pixel clustering engine 212 may identify a second set of additional pixels that may correspond to the surgical gauze 508. Thereafter, the pixel clustering engine 212 may refine the first boundary 518 to generate the second boundary 522, based on the second set of additional pixels 518. The refinement of the first boundary 518 may correspond to the removal of those pixels from the first boundary 518, which may lie outside the surgical gauze 508. In addition, the refinement of the first boundary 518 may also correspond to the inclusion of those pixels to the first boundary 518 that may be a part of the surgical gauze 508, but may not currently lie within the first boundary 518. In accordance with an embodiment, the second boundary 522 may completely encompass the surgical gauze 508. The surgical gauze 508 may be recognized in the input video frame based on the second boundary 522. The output video frame 520 may correspond to a resultant video frame that may be obtained when the second boundary 522 is overlaid over the input video frame to recognize the surgical gauze 508 in the input video frame.

Figure 6:
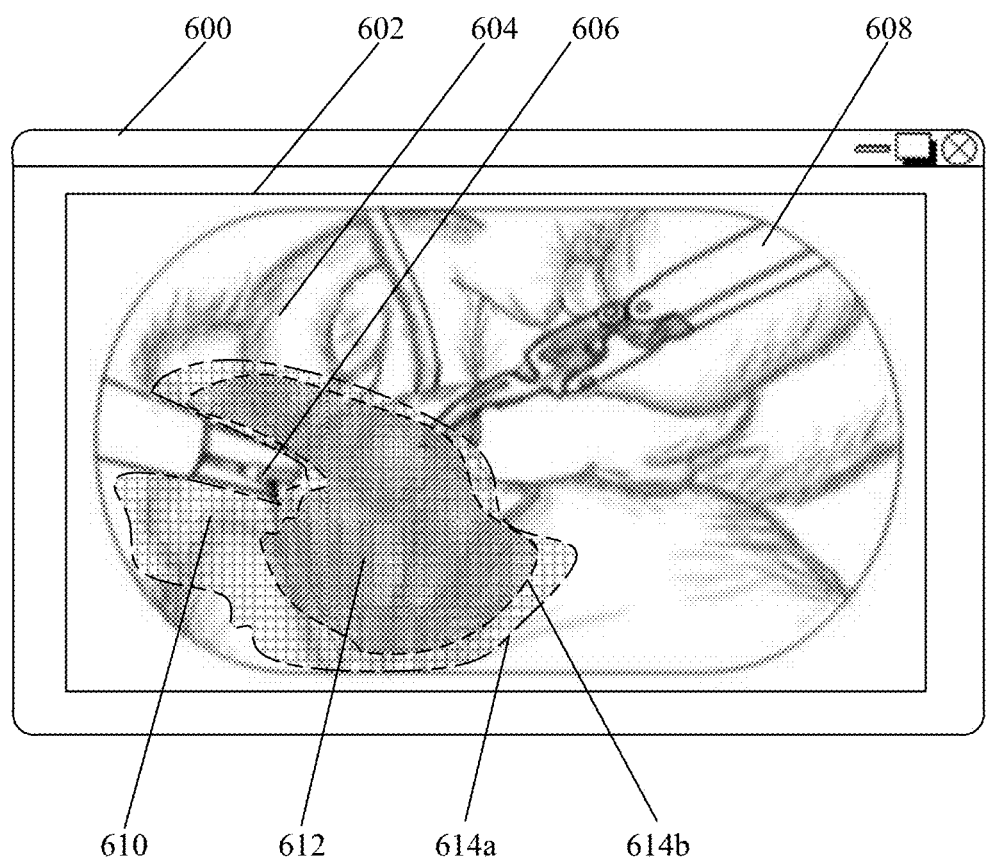
FIG. 6 illustrates an exemplary scenario of a user interface (UI) that may be presented on a user terminal, in accordance with an embodiment of the disclosure.

FIG. 6 illustrates an exemplary scenario of a UI that may be presented on the user terminal 108, in accordance with an embodiment of the disclosure. FIG. 6 has been described in conjunction with elements of FIG. 1. With reference to FIG. 6, there is shown a user interface (UI) 600, which may be presented to the user of the user terminal 108.

In accordance with an embodiment, the UI 600 may be configured to display a surgical scene interface 602 to present one or more video frames to the user. For instance, as shown in FIG. 6, the surgical scene interface 602 may display a video frame that includes a snapshot of a perspective, cross-sectional view of an anatomical region 604 of a patient. The snapshot may be captured while a surgical or diagnostic procedure is performed on the anatomical region 604.

As illustrated in the snapshot, the surgical or diagnostic procedure may be performed by use of one or more surgical gauzes, such as surgical gauze 610, and one or more surgical instruments, such as surgical forceps 606 and an endoscopic surgical instrument 608. For instance, as shown in FIG. 6, a surface of the anatomical region 604 may be held by use of the surgical forceps 606, when the surgical or diagnostic procedure is performed by use of the endoscopic surgical instrument 608.

Further, the surgical gauze 610 may be used to absorb blood or other body fluids that may ooze while the surgical or diagnostic procedure is performed. For instance, the surgical gauze 610 may include a blood-soaked region (depicted by 612), as illustrated in FIG. 6. Although, single surgical gauze and two surgical instruments are shown in FIG. 6, one or more additional surgical gauzes and/or surgical instruments may also be used to perform the surgical or diagnostic procedure, without departure from the scope of the disclosure. As shown in FIG. 6, the snapshot further illustrates a first mask or boundary (depicted by 614a) that may encompass the surgical gauze 610, and a second mask or boundary (depicted by 614b) that may encompass the blood-soaked region 612 of the surgical gauze 610.

In operation, prior to the display of a particular video frame in the surgical scene interface 602, the image-processing server 104 may analyze the video frame. In accordance with an embodiment, the image-filtering engine 210 of the image-processing server 104 may determine a set of pixel characteristics based on color filtering performed on at least a portion of the video frame. Thereafter, the image-filtering engine 210 may detect one or more blocks of pixels that may correspond to a portion of the surgical gauze (such as the surgical gauze 610) in the video frame, based on the determined set of pixel characteristics.

In accordance with an embodiment, the pixel clustering engine 212 of the image-processing server 104 may identify additional pixels that may correspond to a remaining portion of the surgical gauze (such as the surgical gauze 610) in the video frame, based on a plurality of metrics. The additional pixels may be identified by use of a super-pixel clustering technique. Further, the pixel clustering engine 212 may recognize the surgical gauze 610 in the video frame, based on the detection of the one or more blocks that correspond to the portion and the identification of the additional pixels that correspond to the remaining portion of the surgical gauze 610.

In accordance with an embodiment, the surgical scene interface 602 may mask or highlight the surgical gauze 610 recognized in the video frame, while the video frame is presented to the user. For instance, the surgical scene interface 602 may display the first mask or boundary 614a that may encompass the surgical gauze 610 recognized in the video frame. Further, as illustrated in the snapshot of the video frame in FIG. 6, the surgical scene interface 602 may display the second mask or boundary 614b that may encompass the blood-soaked region 612 of the surgical gauze 610 recognized in the video frame.

In accordance with an embodiment, the surgical scene interface 602 may be further configured to present a notification to the user to indicate the recognition of the surgical gauze 610 and the blood-soaked region 612 of the surgical gauze 610, in the video frame. Examples of the notification may include, but are not limited to, an audio alert, a textual alert, a visual alert, and/or a haptic alert. In case the video frame is presented in real time, the surgical scene interface 602 may prompt the user (such as the physician) to take a particular action based on the notification. For instance, the surgical scene interface 602 may prompt the user to adjust the one or more image-capture settings of the image-capturing device.

The surgical scene interface 602 may suggest optimal values for the one or more image-capture settings. The user may adjust the one or more image-capture settings of the image-capturing device, based on the suggested optimal values presented to the user. In addition to adjustment of the one or more image-capture settings of the image-capturing device, the user (such as the physician) may remove or relocate the surgical gauze 610 from the anatomical region 604 of the patient. A person with ordinary skill in the art will understand that the UI 600 has been provided for exemplary purposes and should not be construed to limit the scope of the disclosure.

Various embodiments of the disclosure may encompass numerous advantages. As discussed above, the image-processing server 104 may analyze the one or more video frames to determine the surgical gauze in at least a portion of a video frame in real time. During analysis of the video frame, the image-processing server 104 may initially determine a set of pixel characteristics based on color filtering of the video frame. The image-processing server 104 may detect one or more blocks of pixels that may correspond to a portion of the surgical gauze based on the determined set of pixel characteristics. The portion of the detected surgical gauze may not completely encompass the surgical gauze, and may also include pixels that do not belong to the surgical gauze. The image-processing server 104 may perform a further analysis of the video frame to identify additional pixels that may correspond to a remaining portion of the surgical gauze based on a super-pixel clustering technique. The identification of the additional pixels may include the identification of one or more pixel clusters, based on a plurality of metrics. For instance, the image-processing server 104 may use a spatial metric, a spectral metric, and a weighting parameter to identify the one or more pixel clusters. The use of both spatial and spectral attributes of pixels to identify the pixel clusters may enable an efficient clustering of pixels in the video frame. Thereafter, the image-processing server 104 may recognize the surgical gauze in the video frame based on the detected one or more blocks that correspond to the portion of the surgical gauze and the identified additional pixels that correspond to the remaining portion of the surgical gauze.

During the surgical or diagnostic procedure, the image-processing server 104 may provide a notification to a physician in real time that may indicate the recognition of the surgical gauze. Based on the real-time notification, the physician may remove or reposition the surgical gauze from/within the anatomical region of the patient while the surgical or diagnostic procedure is performed. Further, as discussed, the image-processing server 104 may also enable the physician to adjust the one or more image-capture settings of the image-capturing device, based on the recognition of the surgical gauze in a particular video frame. Such adjustment in the one or more image-capture settings may help in improvement of the quality of the one or more video frames captured by the image-capturing device in real time.

Figure 7:
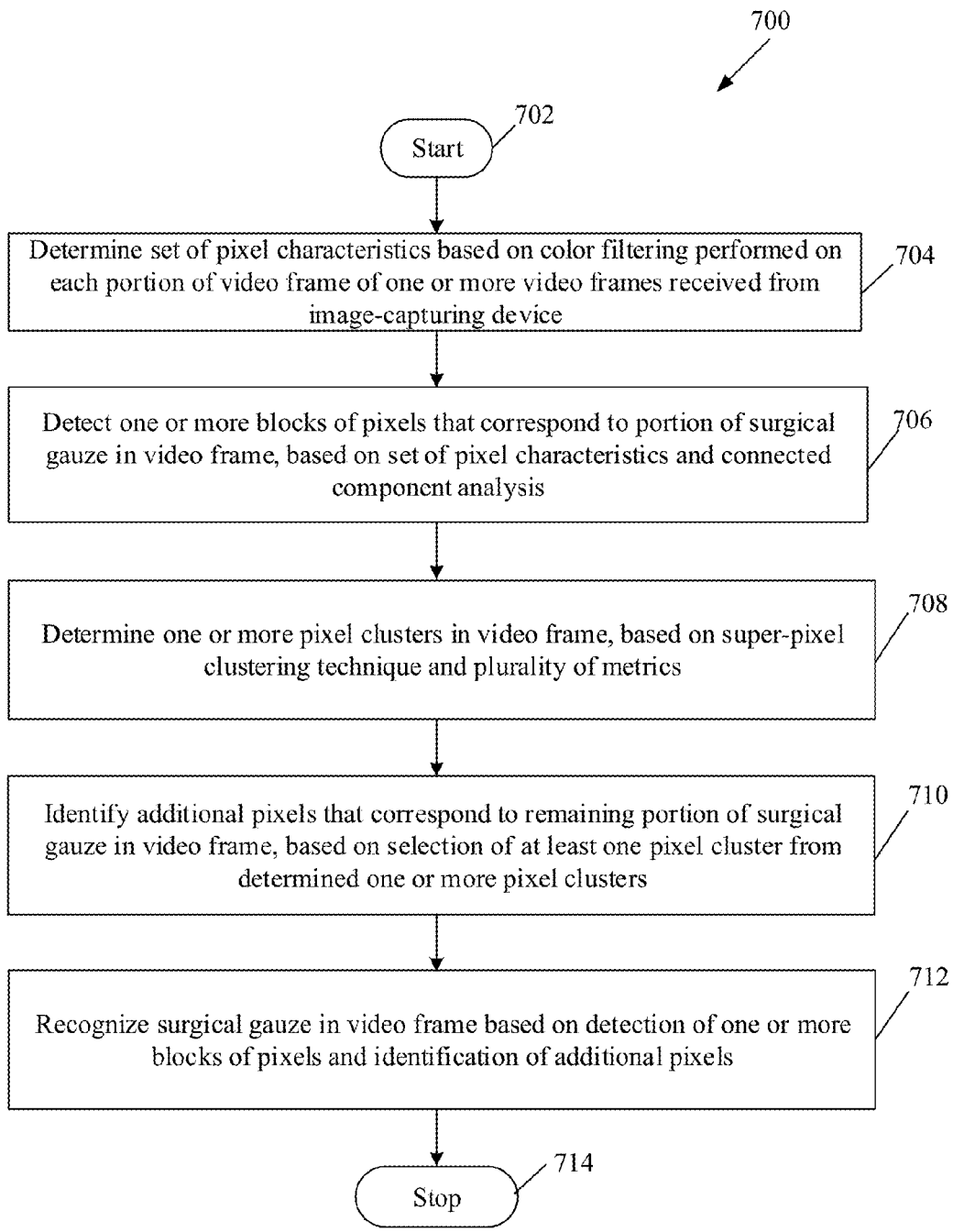
FIG. 7 is a flow chart that illustrates an exemplary method to detect surgical gauze during anatomical surgery, in accordance with an embodiment of the disclosure.

FIG. 7 is a flow chart that illustrates an exemplary method to detect surgical gauze during anatomical surgery, in accordance with an embodiment of the disclosure. With reference to FIG. 7, there is shown a flow chart 700. The flow chart 700 is described in conjunction with FIGS. 1 and 2. The method starts at step 702 and proceeds to step 704.

At step 704, a set of pixel characteristics may be determined. In accordance with an embodiment, the image-filtering engine 210 of the image-processing server 104 may be configured to determine the set of pixel characteristics. The set of pixel characteristics may be determined based on color filtering performed on at least a portion of a video frame from the one or more video frames received from the image-capturing device. The set of pixel characteristics may include, but is not limited to, an edge feature, a shape feature, a texture feature, a size feature, a color feature, an intensity feature, or a density feature. In accordance with an embodiment, the image-filtering engine 210 may perform the color filtering of the video frame based on one or more conditions, such as the conditions, "Condition 1", "Condition 2", "Condition 3", and "Condition 4", as specified in FIG. 2. Further, the image-filtering engine 210 may detect edge pixels in the color-filtered video frame based on the condition, "Condition 5", as specified in FIG. 2. Based on the color filtering and the detection of edge pixels, the image-filtering engine 210 may detect one or more regions of interest in the video frame. The regions of interest may encompass at least a portion of the surgical gauze in the video frame.

At step 706, one or more blocks of pixels that may correspond to a portion of surgical gauze in the video frame may be detected. In accordance with an embodiment, the image-filtering engine 210 may be configured to detect the one or more blocks of pixels, based on the set of pixel characteristics and/or a connected component analysis performed on at least a portion of the video frame. The one or more blocks of pixels may be detected, based on a density analysis of the regions of the interest in the video frame. For instance, the image-filtering engine 210 may generate a confidence map to detect the portion of the surgical gauze based on a density of stripes in each image block in the regions of interest in the video frame. The confidence map may be built based on the condition, "Condition 6", as specified in FIG. 2.

At step 708, one or more pixel clusters may be determined in the video frame. In accordance with an embodiment, the pixel clustering engine 212 of the image-processing server 104 may be configured to determine the one or more pixel clusters in the video frame, based on a super-pixel clustering technique and a plurality of metrics. The plurality of metrics may include a spatial metric and a spectral metric. The pixel clustering engine 212 may determine a Euclidean distance based on the spatial metric, the spectral metric, and a weighting parameter. Thereafter, the pixel clustering engine 212 may determine the one or more pixel clusters in the video frame based on the Euclidean distance between each pair of pixels in the regions of interest of the video frame.

At step 710, additional pixels that may correspond to a remaining portion of the surgical gauze in the video frame may be identified. In accordance with an embodiment, the pixel clustering engine 212 may be configured to identify the additional pixels that may correspond to the remaining portion of the surgical gauze in the video frame. The pixel clustering engine 212 may select at least one pixel cluster from the determined one or more pixel clusters, based on an extent of overlap of each pixel cluster with the detected one or more blocks of pixels and/or the size of each pixel cluster. Thereafter, the pixel clustering engine 212 may identify the additional pixels as the pixels that may correspond to the selected at least one pixel cluster.

At step 712, the surgical gauze may be recognized in the video frame. In accordance with an embodiment, the pixel clustering engine 212 may be configured to recognize the surgical gauze in the video frame. The recognition of the surgical gauze may be based on the detection of the one or more blocks that correspond to the portion of the surgical gauze and the identification of the additional pixels that correspond to the remaining portion of the surgical gauze. Control passes to end step 714.

In accordance with an embodiment of the disclosure, a system to detect surgical gauze during anatomical surgery is disclosed. The system may comprise the image-processing server 104, communicatively coupled to the image-capturing device (not shown in FIG. 1), via the communication network 110. The image-capturing device may be configured to capture one or more video frames during a surgical or diagnostic procedure. The image-processing server 104 may be configured to determine a set of pixel characteristics based on color filtering of at least a portion of a video frame from the one or more video frames. The image-processing server 104 may be further configured to detect one or more blocks of pixels of a portion of surgical gauze in the video frame based on the set of pixel characteristics. In addition, the image-processing server 104 may be configured to identify additional pixels that correspond to a remaining portion of the surgical gauze in the video frame based on a plurality of metrics. Further, the image-processing server 104 may be configured to recognize the surgical gauze in the video frame based on the detection of the one or more block pixels and the identification of the additional pixels.

Various embodiments of the disclosure may provide a non-transitory computer readable medium and/or storage medium, and/or a non-transitory machine readable medium and/or storage medium with a machine code and/or a computer program stored thereon, with at least one code section executable by a machine and/or a computer for detection of surgical gauze during anatomical surgery. The at least one code section in the image-processing server 104 may cause the machine and/or computer to perform the steps that comprise the determination of a set of pixel characteristics based on color filtering of at least a portion of a video frame from one or more video frames. The one or more video frames may be captured by the image-capturing device, which may be communicatively coupled to the image-processing server 104, via the communication network 110. In accordance with an embodiment, one or more blocks of pixels of a portion of surgical gauze may be detected in the video frame based on the set of pixel characteristics. Further, additional pixels that correspond to a remaining portion of the surgical gauze may be identified based on a plurality of metrics. The surgical gauze may be recognized in the video frame based on the detection of the one or more blocks of pixels and the identification of the additional pixels.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system with an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A system for detection of a surgical gauze in an anatomical surgery, comprising:
at least one circuit in an image-processing device communicatively coupled to an image-capturing device,
wherein said image-capturing device captures a video frame,
wherein said at least one circuit is configured to:
determine a set of pixel characteristics based on color filtering of at least a portion of said video frame, wherein said video frame is received from said image-capturing device;
detect at least one block of pixels in said video frame, based on said determined set of pixel characteristics, wherein said at least one block of pixels corresponds to a first portion of said surgical gauze in said at least portion of said video frame;
identify at least one cluster of pixels in said video frame, based on a plurality of metrics, wherein said at least one cluster of pixels corresponds to a second portion of said surgical gauze;
determine a set of pixels in said video frame, wherein said set of pixels is determined based on an extent of overlap of said at least one block of pixels of said video frame and said at least one cluster of pixels of said video frame; and
recognize said surgical gauze in said video frame based on said detection of said at least one block of pixels and said determined set of pixels.

2. The system of claim 1, wherein said set of pixel characteristics comprises at least one of an edge feature, a shape feature, a texture feature, a size feature, a color feature, an intensity feature, or a density feature.

3. The system of claim 1, wherein said plurality of metrics comprises at least one of a spatial metric or a spectral metric.

4. The system of claim 3, wherein said spatial metric corresponds to a geometric distance between coordinates of two pixels in said at least portion of said video frame.

5. The system of claim 3,
wherein said spectral metric corresponds to a lighting-invariant color metric,
wherein said lighting-invariant color metric corresponds to a cosine distance between a plurality of color components of said two pixels in said at least portion of said video frame.

6. The system of claim 3, wherein said at least one circuit is further configured to combine said spatial metric, said spectral metric, and a weighting parameter to determine a Euclidean distance between said two pixels of said at least portion of said video frame.

7. The system of claim 3, wherein said at least one cluster of pixels is identified based on a k-means clustering technique, wherein said k-means clustering technique is based on a combination of said spatial metric, said spectral metric, and a weighting parameter.

8. The system of claim 1, wherein said at least one block of pixels is detected based on a connected component analysis of said at least portion of said video frame.

9. The system of claim 1,
wherein said at least one cluster of pixels in said at least portion of said video frame is identified based on a super-pixel clustering technique.

10. The system of claim 1, wherein said recognition of said surgical gauze in said at least portion of said video frame is based on a combination of said at least one block of pixels and said determined set of pixels.

11. The system of claim 1, wherein at least one image-capture setting of said image-capturing device is adjusted based on said recognition of said surgical gauze in said at least portion of said video frame.

12. The system of claim 11, wherein said at least one image-capture setting comprises at least one of an auto-exposure, an auto-focus, an auto-white-balance, or an auto-illumination.

13. The system of claim 1, wherein said at least one circuit is further configured to display said at least portion of said video frame via a user interface,
wherein said recognized surgical gauze is masked or highlighted in said displayed at least portion of said video frame.

14. The system of claim 1, wherein said at least one circuit is further configured to generate a notification indicative of said recognition of said surgical gauze,
wherein said notification corresponds to at least one of an audio alert, a textual alert, a visual alert, or a haptic alert.

15. A method for detection of a surgical gauze in an anatomical surgery, comprising:
in an image-processing device communicatively coupled to an image-capturing device:
determining a set of pixel characteristics based on color filtering of at least a portion of a video frame,
wherein said video frame is received from said image-capturing device,
wherein said image-capturing device captures said video frame;
detecting at least one block of pixels in said video frame, based on said determined set of pixel characteristics,
wherein said at least one block of pixels corresponds to a first portion of said surgical gauze in said at least portion of said video frame;
identifying at least one cluster of pixels in said video frame, based on a plurality of metrics,
wherein said at least one cluster of pixels corresponds to a second portion of said surgical gauze;
determine a set of pixels in said video frame, wherein said set of pixels is determined based on an extent of overlap of said at least one block of pixels of said video frame and said at least one cluster of pixels of said video frame; and
recognizing said surgical gauze in said at least portion of said video frame based on said detection of said at least one block of pixels and said determined set of pixels.

16. The method of claim 15, wherein said set of pixel characteristics comprises at least one of an edge feature, a shape feature, a texture feature, a size feature, a color feature, an intensity feature, or a density feature.

17. The method of claim 15, wherein said plurality of metrics comprises at least one of a spatial metric or a spectral metric.

18. The method of claim 17, further comprising combining said spatial metric, said spectral metric, and a weighting parameter to determine a Euclidean distance between two pixels of said at least portion of said video frame.

19. The method of claim 18, wherein said at least one cluster of pixels is identified based on a k-means clustering technique, wherein said k-means clustering technique is based on said Euclidean distance.

20. The method of claim 15, wherein said at least one cluster of pixels in said at least portion of said video frame is identified based on a super-pixel clustering technique.

21. The method of claim 20, wherein said recognition of said surgical gauze in said at least portion of said video frame is based on a combination of said at least one block of pixels and said determined set of pixels.

22. A non-transitory computer-readable storage medium having stored thereon computer executable instructions that, when executed by a processor, cause a computer to perform operations, said operations comprising:
determining a set of pixel characteristics based on color filtering of at least a portion of a video frame,
wherein said video frame is received from an image-capturing device,
wherein said image-capturing device is communicatively coupled to said computer,
wherein said image-capturing device captures said video frame;
detecting at least one block of pixels in said video frame, based on said determined set of pixel characteristics,
wherein said at least one block of pixels corresponds to a first portion of a surgical gauze in said at least portion of said video frame;
identifying at least one cluster of pixels in said video frame, based on a plurality of metrics,
wherein said at least one cluster of pixels corresponds to a second portion of said surgical gauze;
determine a set of pixels in said video frame, wherein said set of pixels is determined based on an extent of overlap of said at least one block of pixels of said video frame and said at least one cluster of pixels of said video frame; and
recognizing said surgical gauze in said at least portion of said video frame based on said detection of said at least one block of pixels and said determined set of pixels.

* * * * *